US006766682B2

United States Patent
Engle et al.

(10) Patent No.: US 6,766,682 B2
(45) Date of Patent: Jul. 27, 2004

(54) PRECISE MEASUREMENT SYSTEM FOR BARRIER MATERIALS

(75) Inventors: Frank W. Engle, Oro Valley, AZ (US); Clark I. Bright, Tucson, AZ (US)

(73) Assignee: Desert Cryogenics LLC, Tucson, AZ (US)

(*) Notice: Subject to any disclaimer, the term of this patent is extended or adjusted under 35 U.S.C. 154(b) by 40 days.

(21) Appl. No.: 10/037,602

(22) Filed: Oct. 19, 2001

(65) Prior Publication Data

US 2003/0074954 A1 Apr. 24, 2003

(51) Int. Cl.⁷ .............................................. G01N 15/08
(52) U.S. Cl. ...................................................... 73/38
(58) Field of Search ............................................ 73/38

(56) References Cited

U.S. PATENT DOCUMENTS

| | | | |
|---|---|---|---|
| 3,590,634 A | * 7/1971 | Pasternak et al. | 73/38 |
| 3,718,434 A | * 2/1973 | Pierce | 73/38 |
| 3,926,561 A | * 12/1975 | Lucero | 73/38 |
| 4,944,180 A | 7/1990 | Tou et al. | 73/38 |
| 5,591,898 A | 1/1997 | Mayer | 73/38 |
| 5,725,909 A | 3/1998 | Shaw et al. | |
| 5,981,059 A | 11/1999 | Bright et al. | |
| 6,009,743 A | 1/2000 | Mayer | 73/38 |
| 6,083,628 A | 7/2000 | Yializis | |
| 6,268,695 B1 | 7/2001 | Affinito | |

OTHER PUBLICATIONS

"Thin Film Technology", Vacuum Technology & Coating, pp. 20–24, Oct., 2000.
"Measuring Oxygen Permeability through Today's Packaging Barriers" by Robert L. Demorest, published by Modern Controls, Inc., not dated.
"Comperative Study of Oxygen Permeation through Polymers and Gas Barrier Film", paper presented 2000 Society Of Vacuum Coaters, Apr. 15–20, 2000.
ASTM Spec D–1434–82 (Reapproved 1998)—"Standard Test Method for Determining Gas Permeability Characteristics of Plastic Film and Sheeting".
Brochure entitled "System for Measuring Water Vapor Transmission Rates", published by Modern Controls, Inc. (MOCON), not dated.

* cited by examiner

Primary Examiner—Daniel S. Larkin
(74) Attorney, Agent, or Firm—Stanley Z Cole

(57) ABSTRACT

A system is provided for measuring transmission characteristics of a gas of interest through a barrier material wherein a sealed test gas chamber is provided on one side of the barrier material and an aligned sealed measurement chamber is provided on the opposite side of the barrier material. A rough vacuum is pulled in the test gas chamber and a high vacuum pulled in the measurement chamber to establish a set pressure differential therebetween. A mass spectrometer having partial gas sensitivities of $5 \times 10^{-4}$ Torr or lower in fluid communication with the measurement chamber determines permeation of the test gas of interest through the barrier material.

10 Claims, 8 Drawing Sheets

PRECISE MEASUREMENT SYSTEM FOR BARRIER MATERIALS

This invention was made with Government support under Agreement No. MDA972-93-2-0014, awarded by DARPA. The Government has certain rights in the invention.

This invention relates generally to method and apparatus for determining gas transmission characteristics of materials, and more particularly, the gas permeability characteristics of barrier materials.

The invention is specifically applicable to and will be described with particular reference to an instrument for measuring oxygen and water vapor permeability of barrier materials for electronic displays such as organic light emitting diodes and field emission displays requiring highly sensitive permeation measurements. However, those skilled in the art, while recognizing the benefits of the invention for precisely determining gas transmission characteristics in a sensitive application, will also recognize that the invention is not necessarily limited to barrier materials but could be applied to any permeable material where the permeability of the material is desired to be determined in a short time, nor is the invention necessarily limited to detecting elemental or simple compound gases, but could have application for detecting transmission characteristics of hydrocarbons or gaseous organic compounds.

BACKGROUND

The food industry has long recognized that the shelf life of food is correlated to the solubility and diffusivity characteristics of food packaging material. It is well known that native (i.e., uncoated) plastics are very permeable to water and oxygen. Testing standards have long been established to determine permeability characteristics of packaging material. Barrier coatings have been developed to retard permeability of oxygen and water vapor through the plastics. It is to be recognized that the shelf life of food is typically measured in days. For example, 30 days is generally regarded as an acceptable shelf life for pharmaceuticals or packaged consumerable goods, such as potato chips.

In marked contrast, displays, such as television screens or flat panel displays on a laptop computer, have a significantly longer operating life. For example, display requirements typically specify that the brightness of the display will be at least 50% of its original brightness after 10,000 hours of use. However, for displays which are degraded by trace amounts of oxygen or water vapor, a serious failure rate will occur at much less than the expected 10,000 hour lifetime.

Today's display devices require fabrication using plastic substrates because plastic is lightweight, impact resistant, and can produce glass light transmission characteristics. Particularly, microelectronic devices, organic light emitting devices (OLED), and field emission display (FED) are being developed for flat display panel applications as well as electronic encapsulation packaging. Because of the high sensitivity of these materials to oxygen and water, especially formulated barrier coatings, sometimes termed engineered plastic substrates, are being developed. The barrier coatings are thin film barriers, typically consisting of metal (AL) or oxide ($SiO_2$, $AL_2O_3$) having layer thickness of only about 20 to 30 nanometers and applied to plastic substrates by vacuum deposition techniques. A plurality of thin, specially formulated barrier films are applied to flexible plastic webs, films, or sheets significantly decreasing permeability of barrier coated plastics.

Uncoated plastics, whose properties are otherwise appropriate for panel displays, have permeabilities for water in the vicinity of 10 $g/m^2$/day. Experimental estimates have been made which suggest that a desirable goal of about $10^{-6}$ $g/m^2$/day for water and $10^{-6}$ $cc/m^2$/day for oxygen is desired as a design permeation goal for plastic barrier materials used in panel display applications under discussion. Currently, within the trade, the best commercially available instrument for measuring gas permeabilities has a sensitivity limit of about $10^{-3}$ $g/m^2$/day for water and about $10^{-3}$ $cc/m^2$/day for oxygen. Reference can be had to an article entitled "Thin Film Technology", pages 20–24, in the October, 2000 issue of *Vacuum Technology & Coating* in which target permeation rates at this level are specified with maximum sensitivity of current measuring instruments cited as being limited to the order of 0.005 $cc/m^2$/day. For reference and comparison purposes, converting the sensitivity achieved by the prior art of 0.005 $cc/m^2$/day to standard cc's/second/sample (i.e., 0.005 cc's×10,000/area×86,400/day) yields a published, prior art maximum sensitivity of 4,320,000 cc's/second/$cm^2$. In any event, currently available instruments do not have the sensitivity needed to determine the suitability of the specially developed engineered plastic substrates for display panel applications.

An article published by *Modern Controls Inc.*, entitled "Measuring Oxygen Permeability through Today's Packaging Barriers", by Robert L. Demorest, describes the testing procedures commonly used in the packaging industry for measuring oxygen permeability, or more correctly, oxygen transmission rates. In the article, it is noted that prior to 1975, ASTM specification D-1434 was commonly used. In the ASTM D-1434 test, the plastic sample is mounted in a gas transmission cell to form a sealed semi-barrier between two chambers. One chamber contains the test gas at a specific high pressure and the other chamber, at a lower pressure, receives the permeating gas. Two procedures are set forth. In one procedure, the lower pressure chamber is maintained near atmospheric pressure and the transmission of the gas through the test specimen is indicated by a change in volume. In the second test procedure, the lower pressure chamber is initially evacuated and the transmission of the gas through the test specimen is indicated by an increase in pressure as measured by a manometer. Specifically, an initial vacuum is pulled in both chambers. The vacuum lines are closed and one of the chambers is flushed with a test gas. After some time (in the hours) has passed to achieve a steady state condition, the manometer is read over a series of time intervals to determine permeance, etc. The vacuum test is a static, not dynamic, test because the lines are closed. This gives a coarse instrument which is slow in response. Thus, the pressure test method or Dow Cell technique, is a static determination of the change of pressure in the test chamber after steady state conditions have been established from which information about the permeability of the plastic is obtained. The time of the test takes hours and the test is destructive. The sensitivity is limited. The *Modern Controls* article noted that the test was seldom capable of testing oxygen barriers below 1.00 $cc/m^2$/day.

The current method in wide use today was published by ASTM as specification D-3985, in 1981. In this method, the sample to be tested is clamped between two chambers as discussed above, but, one side is exposed to a gently flowing oxygen stream while the other chamber is exposed to a nitrogen stream. As oxygen molecules permeate through the sample into the nitrogen stream, they are picked up and carried into a coulometric sensor. This sensor causes a release of 4 electrons electrochemically for every oxygen molecule which passes through it. The electrons form a current passed through a resistor creating a voltage which can be recorded. Such tests are also subject to lengthy time periods to achieve steady state conditions and the measurements are lacking in sensitivity because the permeant gas is only fractionally present in the sample.

In the literature, a paper entitled "Comparative Study of Oxygen Permeation Through Polymers and Gas Barrier Films", 2000 Society of Vacuum Coaters, presented Apr. 15–20, 2000, at the 43rd Annual Technical Conference Proceedings, discussed four different methods which were experimented with to determine oxygen transmission rates in barrier films. The four methods investigated included Oxtran, which is the standard method used to measure oxygen with the coulometric sensor discussed above. The second method was described as a time lag method which is generally similar to the D-1434 ASTM spec. In the time lag method, the sample sheet is clamped between two vessels evacuated to a pressure of $1 \times 10^{-4}$ Pa. Gas was then bled into the upper vessel at atmospheric pressure and the pressure in the lower vessel was monitored as a function of time using a Penning gauge. As in the ASTM spec., once steady state conditions were reached, the pressure increase per time is proportional to the gas transmission. The third method was described as a GTR10 method which clamped the film into the two chamber arrangement discussed above. A vacuum vessel was provided adjacent the space under the film and the space and vacuum vessel were evacuated to $1 \times 10^{-4}$ pa. A feeding side of the membrane was then exposed to a gas at 1–3 atmospheres and the gas permeating through the semi permeable barrier was collected in the vacuum vessel. After a set time, the vacuum vessel was cut off from the gas supply and the collected gas streams passed through to a chromatograph which measures the heat conductivity to determine the amount of gas. The fourth test procedure was described as a mass spectrometric method. In this method, a gas cell was placed in a UHV system ($10^{-10}$ mbar) to face the entrance aperture of a mass spectrometer. The gas cell contained a fixed volume of gas that had an exposed diameter of 4 mm which was covered by the barrier specimen. The partial pressure of the permeant gas was then measured as a function of time and from the time constant of drop of partial pressure, the gas transmission was calculated.

The article stated that the partial pressure versus time curve measured by the mass spectrometer had insufficient slope; that going to smaller gas transmission rates made measurements by the mass spectrometer difficult and concluded that the mass spectrometer had a relatively big margin of error because of its small sample size.

Within the patent literature there is disclosed an outgasing technique in U.S. Pat. No. 5,591,898 and further refined, for continuous sensing application, in U.S. Pat. No. 6,009,743. In this technique, the plastic barrier saturated with a test gas and the outgasing of a plastic is measured to construct a degassing rate of decay curve which is correlated to permeability, etc. The test arrangement is the two chamber type with a neutral gas containing the out gas detected by a conventional sensor, such as an oxygen sensor or the like. Because the permeant gas is diluted by the neutral gas, there are limits to the sensitivity of this approach.

U.S. Pat. No. 4,944,180 discloses a somewhat conventional two chamber test box arrangement with a neutral or carrier gas flowing through one chamber and a permeant gas flowing at positive pressure through the other chamber. A long interface tube connects the chamber receiving permanent gas transmitted through the test specimen to a mass spectrometer. This arrangement has a potential for sensitive measurements because of the sensitivity of the mass spectrometer. However, the test chambers are at positive pressure and the transmitted permeant gas is diluted by the neutral or carrier gas which renders its use for low atomic numbered gases difficult. In addition, a capillary interface is required.

In summary, the prior art has developed and is developing barrier materials needed for long life in applications which are extremely sensitive to select gases or vapors, such as oxygen and water vapor. The multi-layer barrier materials under discussion are required to have such reduced permeability or low transmission rates that instruments available today or discussed in the prior art do not have sufficient sensitivity to allow meaningful testing of the new barrier materials. In addition, most, if not all, of the prior art systems discussed above establish permeability and gas transmission rates on a relative scale. That is, if material "A" exhibits a first reading and material "B" exhibits a second higher reading, then permeability of material "B" can be established as a function of the permeability of material "A". Calibration can then be established by setting a base material "A" from which other measurements can be compared. Calibration as an absolute or standardized value does not occur. In addition, most of the tests require that an equilibrium be established on both sides of the barrier material before meaningful measurements can be taken which increases the time of the test. To some extent, test time is reduced by measuring the out gassing characteristics of the material. However, the material must still be saturated to some extent with the permeant gas before the measurements can be taken. Still further, many of the test systems discussed are destructive in nature and do not permit non-invasive sampling of production barrier material.

SUMMARY OF THE INVENTION

Thus, it is one of the main objectives of the present invention to provide a system, method, and apparatus, which can measure the permeability of barrier materials with a higher degree of sensitivity than that of currently available instruments. This feature, by itself or in combination with other objects of the invention discussed below, forms one of the underpinnings of the invention.

This object along with other features of the invention is achieved in a system for measuring transmission of a selected gas, vapor, or aroma of interest through a barrier material to establish permeability which, in the preferred embodiment, includes a test box having first and second facing surfaces confronting one another with a continuous seal extending from one of the facing surfaces to circumscribe a sealable area. A clamp mechanism is actuable from an open position to a clamped or closed position whereat the first facing surface contacts one side of the barrier material to form a test gas chamber extending from one side of the material and a seal in the second facing surface sealing engages the opposite side of the barrier material to form a sealed measurement chamber extending from the opposite side of the material. Importantly, the sealable area bounded by the seal in the second facing surface defines a measurement sealable area that spans a distance sufficient to permit, as a function of the barrier characteristics of the barrier material, a uniform diffusion of the gas under a "hard" vacuum through the barrier material into the measurement chamber. Preferably, a continuous seal is provided for the test gas chamber so that both measurement and test gas chambers are sealed.

The system includes the test gas chamber having an inlet port connected to a source of the gas of interest, an outlet port, and a flow valve connected to a source of vacuum for controlling flow of the gas of interest into and out of the test gas chamber. A second vacuum system is provided in valved communication with the measurement chamber for drawing a vacuum of at least about $5 \times 10^{-4}$ Torr in the measurement chamber when actuated (In practice, a pressure less than this value can be established. However, a pressure of at least this value can be readily obtained and will produce superior instrument results when compared to the prior art.) A mass spectrometer in fluid communication with the measurement chamber is provided for analyzing the concentration of the gas of interest diffused into the measurement chamber at any given time. A mechanism is provided for controlling the mass spectrometer, the vacuum pump and vacuum system, and the flow valve to permit sampling of the concentration of the gas in the measurement chamber at set intervals, whereby the differential in pressure between the vacuum in the test chamber and measurement chamber is set to be sufficient to permit diffusion of the selected gas through the barrier material without permanently distorting the barrier material while establishing sufficiently high vacuum levels for the mass spectrometer to analyze the partial pressure of the selected gas transmitted to the measurement chamber to achieve highly sensitive and accurate measurements.

A significant feature of the invention resides in the fact that the mass spectrometer functions by continuously pumping the measurement chamber at a high vacuum to determine the content of a gas or vapor of interest at any selected time while the test gas chamber is continuously circulating a fresh supply of a gas or vapor of interest to the test gas chamber. The dynamic conditions on both sides of the barrier material allow the barrier material to achieve saturation or equilibrium in an optimally fast time when contrasted to prior art static test procedures. Additionally, in the preferred embodiment, a high vacuum, constant speed (550 l/sec) turbomolecular pump produces a high vacuum (low pressure) resulting in a good signal-to-noise ratio. Accurate determination of gas transmission rates not only at saturation or equilibrium, but also during the time the barrier material is transitioning from an unsaturated to a saturated state is possible. Significantly, because accurate measurements can be taken during the transition time, any number of known predictive modeling techniques can be used to predict equilibrium or establish pass/fail criteria so that testing does not have to extend to the time whereat equilibrium is achieved.

In accordance with another feature of the invention, the system includes a roughing vacuum pump valved to initially draw a vacuum in both the test chamber and measurement chamber, a molecular pump backed with a roughing pump valved to draw a hard vacuum in the measurement chamber and the control mechanism insures the integrity of the test gas chamber and measurement chamber before drawing and after drawing a hard vacuum in the measurement chamber whereby the measurements obtained from the mass spectrometer are assured as to accuracy.

In accordance with another aspect of the invention, the system includes in the preferred embodiment, as a source for the vapor of interest, a container for water, a heater for heating the water to a temperature of approximately 20 to 75 degrees C. (a temperature range known to be conducive to produce vapor under vacuum although not essential for formation of water vapor to practice the invention), and an agitator to produce water bubbles when the container is subjected to a rough vacuum from the rough vacuum pump whereby water vapor is produced and the transmission of water vapor is correlated by the control mechanism to the life of the barrier material at relative humidity levels.

In accordance with yet another object of the invention, the gas of interest is selected preferably to have an atomic mass of 50 or less which is selected because of the ability of gases within this range to diffuse or permeate rapidly through micro-cracks and/or pin holes in barrier materials of the type now being applied to OLEDs, FEDs, etc. (In accordance with the broader inventive scope, the gas of interest can include organics such as aromatics and the mass is limited by the sensitivity of the mass spectrometer which can extend to a gas of interest having an atomic mass of 200 or less.)

In accordance with another aspect of the invention, the chambers are fitted with heaters whereby the excitation of the gas of interest and its transmissibility through the barrier material is increased to reduce the test time.

In accordance with another specific object of the invention, the gas of interest other than oxygen and water vapor includes an inert gas, preferably helium and the control mechanism correlates the transmissibility of helium through the barrier material to the traditional gases of interest, such as oxygen, and humidity whereby a non-invasive measurement is obtained and the measurement is calibrated to a NIST standard to assure an absolute value.

In accordance with yet another feature of the invention, the system includes a plurality of seals establishing a like plurality of pairs of measurement and test gas chambers longitudinally spaced from one another with each test gas chamber in each pair of chambers having its inlet port in valved fluid communication with a common gas manifold and its outlet port in fluid communication with a common exhaust manifold. The exhaust manifold is valved to an atmospheric vent and to the roughing vacuum pump and the gas manifold is in valved communication with a plurality of source gases whereby one or more of the source gases may be valved into fluid communication from the common manifold with select test gas chambers while the rate of flow of one or more of the source gases into each test gas chamber may be individually set by the control mechanism so that a number of gases of interest may be simultaneously tested and/or the differential pressures in chamber pairs for a select gas of interest may be varied to produce even faster test times and/or multiple gases of interest may be evaluated in combination in select chamber pairs.

In accordance with yet another object of the invention, the barrier material in one embodiment of the invention is in a roll form and the system has a payout reel at one longitudinal end thereof and a take-up reel at the opposite longitudinal end and the control mechanism includes a programmed routine implemented by a computer for synchronizing the rotation of the reels to sequentially move the roll longitudinal set distances relative to the box after a plurality of the test gas and measurement chamber pairs have simultaneously analyzed the gas transmission characteristics of the selective gases of interest over a segment of the roll whereby the production barrier material may be non-invasively tested with test data recorded for quality control purposes. This technique may be incorporated in an on-line or post production system for testing. Other implementations of this method could use an in-line or conveyor transport system for sheet material. A hybrid system which uses roll to roll handling, then sheets the material, and handles the sheets, is also suitable for production testing.

In accordance with a specific but important feature of the invention, the system of the invention may optionally include a porous support for supporting the barrier material against excessive deflection into the measurement chamber, preferably including a grid having a lattice structure lacking sharp edges whereby differential vacuum levels of a sufficient level may be maintained between the test gas chamber and the measurement chamber without damaging the barrier material. Because the grid is positioned in the measurement chamber which has less pressure than the test gas pressure, test gas flow into the measurement chamber is not impeded should the barrier material contact the grid and special calibration techniques are not necessary.

In accordance with another feature of the invention, a method for determining the transmission characteristics of at least one gas or vapor through plastic barrier materials of the type used for encapsulating electronic displays including organic light emitting diodes and field emission displays is provided which includes the steps of:

a) forming a vacuum across the barrier material by establishing a sealed test gas chamber extending from one side of the barrier material and a sealed measurement chamber extending from the opposite side of the barrier material and the sealed chambers extend over a surface area of the material of at least about 10 cm$^2$ whereby sufficient material area is provided to assure average gas transmission characteristics through the barrier material;

b) establishing a rough vacuum across the barrier material between the measurement and test gas chambers;

c) establishing a high vacuum in the measurement chamber;

d) measuring the background partial pressure of the measurement chamber under said high vacuum;

e) continuously flowing the gas of interest through the test gas chamber; and f) continuously measuring partial pressure of the gas of interest in the measurement chamber over time to correlate the change in partial pressure to the permeability of said material. With this method, fast testing times inherently occur because saturation of the barrier material by the gas of interest is not necessary to establish transmissibility characteristics of the gas of interest through the barrier material.

In accordance with a specifically important feature of the invention, the partial pressure of the measurement chamber is measured by a mass spectrometer having a sensitivity of at least about $2 \times 10^{-4}$ Torr. The mass spectrometer is calibrated to a NIST standard whereby the partial pressure measurements recorded by the mass spectrometer during testing establish absolute transmission test values.

In accordance with another important aspect of the invention, full testing of a barrier material can occur by allowing the test to proceed to an equilibrium condition whereat the flow of a test gas through the barrier material is constant. The sensitivity of the inventive instrument provides for the desired accuracy to permit evaluation of the barrier material. However, the sensitivity of the instrument allows for an accurate transmission determination of the gas of interest through the barrier material during the entire test time and prior to the sample reaching equilibrium. Because the transmission graph is accurately determined throughout the time it takes for the gas or vapor of interest to reach equilibrium, the invention contemplates the use of any known curve fitting or statistical analysis methodologies to establish pass/fail criteria prior to the time the gas transmission reaches equilibrium. Accordingly, the test time in the sense of at least pass/fail can be significantly reduced.

In accordance with another aspect of the invention, which is somewhat distinct, but related to several inventive features, the gas of interest is chosen as helium. The system uses a mass spectrometer calibrated with helium to establish an absolute value when the mass spectrometer is used to measure the gas transmission characteristics of helium. This value, in turn, is correlated to any gas of interest. More specifically, the instrument is operated in a normal manner to establish a transmission rate reference curve for any desired gas of interest and a correlation between the transmission graphs is established (such as that resulting from the superposition of one graph over the other graph) to determine if test specimens meet pass/fail criteria for any given gas of interest on the basis of sensing helium transmission through the specimen. In fact, several gases of interest can be correlated on the basis of a single helium gas transmission test. Because of the light weight of helium, the transmission of helium through the barrier material will quickly establish equilibrium, or a discernible trend to equilibrium to further reduce test time. Because the mass spectrometer is calibrated with helium to an absolute standard (NIST), the measurement, although a correlation, is based on an absolute and not relative measurement values. Finally, helium is a non-invasive gas allowing it to be used for testing on production samples without saturating the material or sample with a gas that is damaging to the display life.

In summary, some of the significant objectives of the present invention is the provision of a system for measuring gas transmission rates (permeability) of a gas/vapor or gases/vapors of interest through a permeable material having one or more or any combination of the following:

a) dynamic testing by continuously flowing test gas through test gas chamber in an instrument capable of measuring gas transmission by continuously drawing and analyzing gas transmitted through the barrier material to a measurement chamber and present a more accurate and more responsive test measurement than possible in static tests;

b) suitable for quantitative testing of engineered plastic substrates, i.e., barrier coated plastic substrates, as well as other permeable materials;

c) sensitivities that can exceed $10^{-6}$ cc/m$^2$/day (as high as $10^{-8}$ cc/m$^2$/day) for a number of gases of interest and/or $10^{-6}$ g/m$^2$/day of water vapor;

d) measurements that can be correlated to an NIST standard and therefore indicative of an absolute measurement;

e) fast test times;

f) potential for non-invasive or non-destructive material testing so that the instrument can be used to continuously measure and record data for production barrier material;

g) simultaneous measurement of a plurality of singular gases of interest or a plurality of gases of interest or a singular gas of interest at multiple stations at set varying conditions for a reduction in test time;

h) ability to determine the rate of transmission of any number of gases of interest thereby allowing for potential of developing correlations between any given gas to any other gas of interest to minimize testing time;

i) ability to separately determine humidity affects on the material thereby avoiding prior art limitations which have to set a controlled humidity level at which the material is tested for permeability;

j) separately control excitation activity of a gas of interest by heat to further reduce test time; and/or k) reduce test time by partial pressure measurement via a mass spectrometer which can be taken before the material reaches saturation limits.

These and other objects, features, and advantages of the present invention will suggest themselves to those skilled in the art upon reading and understanding the Detailed Description of the Invention set forth below.

BRIEF DESCRIPTION OF THE DRAWINGS

The invention may take form in certain parts and arrangement of parts, a preferred embodiment of which will be described in detail and illustrated in the accompanying drawings which form a part hereof and wherein.

DETAILED DESCRIPTION OF THE INVENTION

Figure 1:
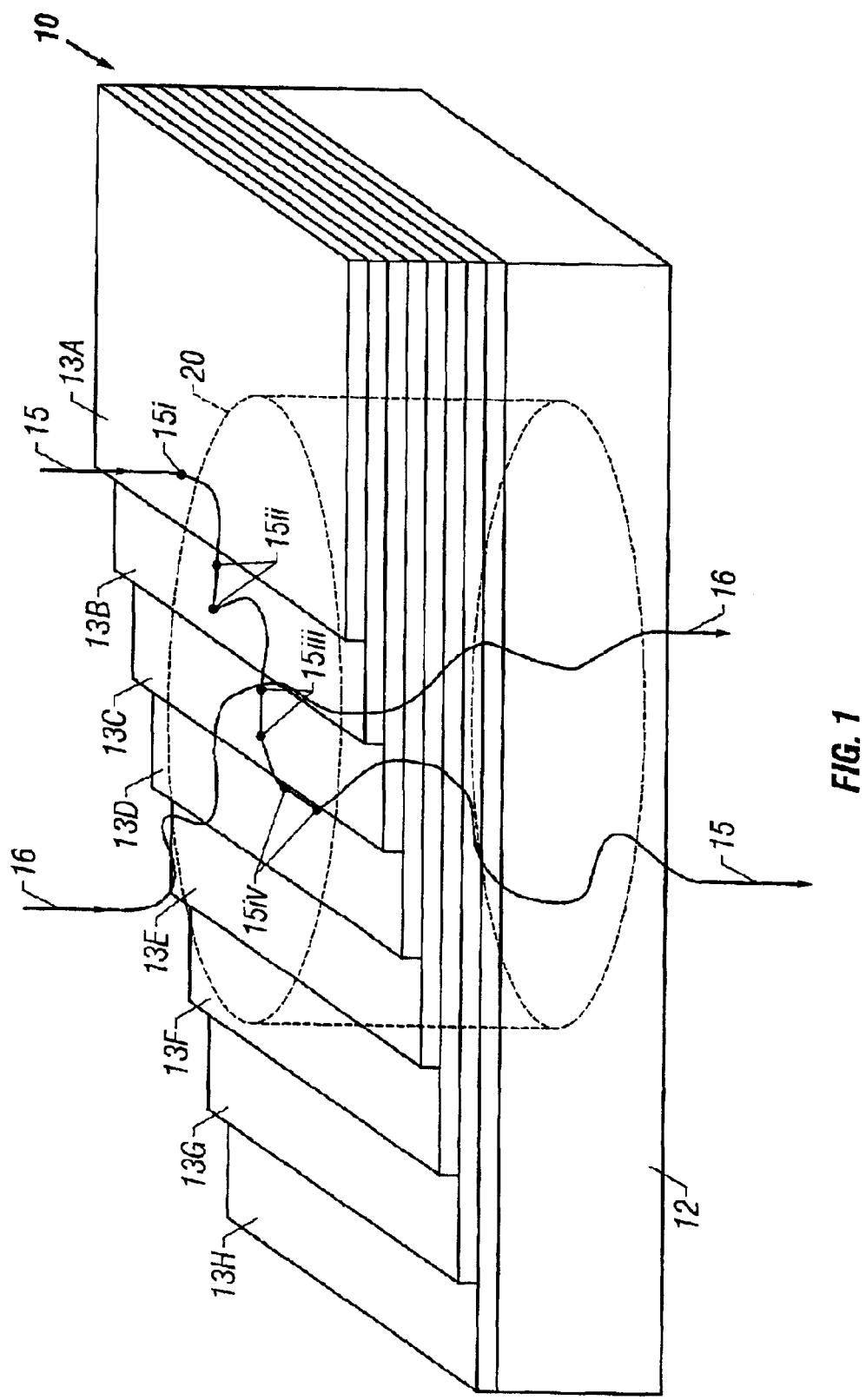
FIG. 1 is a schematic representation of a barrier material.

Referring now to the drawings wherein the showings are for the purpose of illustrating a preferred and alternative embodiments of the invention only, and not for the purpose limiting same, there is schematically shown in FIG. 1 a representation of a barrier material 10.

For consistency in terminology and as a matter of definition, when used herein the following words, terms, or terminology has the following meanings:

"Barrier material" means a gas permeable substrate which has more than one layers or coatings of a material applied to one or both sides or surfaces of the substrate which layers or coatings have the effect of reducing permeance or gas transmission through the substrate. The invention has been constructed in the preferred embodiment to test polymeric substrates having thin metal oxide or ceramic oxide coatings of about 1 micron in thickness, referred to in the Background as engineered plastic materials which now or in the future may be developed for the reasons discussed above. However, "barrier material" as defined includes but is not limited to such engineered plastic materials. Substrates other than plastic, such as glass or non-plastic fibers having any type of coating(s), are intended to fall within the definition of a barrier material.

"High vacuum" is intended to cover vacuum at least as low as $10^{-4}$ Torr or lower (i.e., lower pressures). In the preferred embodiment and particularly for testing engineered plastic materials, high vacuum levels (pressures as lows as) of about $10^{-7}$ to $10^{-8}$ Torr to as low as (pressures as low as) $10^{-11}$ Torr are used to analyze transmission rates of specific gases of interest having relative low atomic mass.

"Low vacuum" or "roughing vacuum" is intended to cover rough vacuum levels as customarily used in the trade of about $1\times10^{-3}$ Torr to 760 Torr.

"Mass spectrometer" or "residual gas analyzer" means any conventional, preferably tunable, mass spectrometer capable of resolving, distinguishing, or measuring atomic masses in the 0–50 atomic mass unit (amu) range with sensitivities of $5\times10^{-4}$ Torr or greater, preferably sensitivities of $10^{-8}$ to as low as $10^{-11}$ Torr. As a matter of definition, the invention when applied to plastic material contemplates mass spectrometers capable of distinguishing gases or vapors having atomic masses between 0–50 amu. However, in accordance with a potentially broader scope of the invention resulting from its dynamic characteristics, mass spectrometer's having higher amu ranges may be used with organic gases or vapors (HCs, aromatics, etc.) having significantly higher atomic mass units than the 0–50 range established for the preferred embodiment, i.e., 0–200 amu.

"Gas of interest" always means a substance which is a specific gas at ambient temperature whether the gas is a compound or an elemental gas. However, the "gas of interest" phrase is also used in a general sense to mean any gaseous substance including vapors, such as water vapor, or even gasified solids. In short, the invention is concerned with measuring permeation of gaseous substances through barrier material and "gas of interest" if not otherwise qualified by additional phrases is intended to cover all substances which are in a gaseous form when tested by the inventive system.

"High vacuum pump" means, in accordance with the broader aspects of the invention, any pump or pump system capable of pulling a high vacuum as defined or higher (lower pressure) i.e., $10^{-4}$ Torr or lower Torr and preferably the pump is capable of exhausting to atmosphere. In the preferred embodiment, the high vacuum pump selected is a turbo molecular pump which is advantageous in that it has a predictable pumping speed for all gases of interest, which are relatively light in the application of the preferred embodiment. That is, a turbomolecular pump is preferred in the application under discussion because speed is not a factor, all gases of interest can pump relatively uniformly without fear of contamination and maintenance and operating issues related to the mass spectrometer (which may be a by-product of other types of pump) are minimized. Again, the definition of a high vacuum pump includes pumps other than a turbo molecular pump capable of pulling the vacuum specified and does contemplate the use of diffusion pumps. In the preferred embodiment of the invention set forth herein, a diffusion pump was not selected because of potential problems that could arise with the liquid nitrogen trap used with such pumps. However, a diffusion pump will work. Both diffusion and turbo molecular pumps use backing or roughing pumps so that the high vacuum pumps are capable of exhausting to atmosphere. In contrast, capture pumps, such as ion or cryogenic pumps, while capable of pulling the high vacuum required are really not suited for the inventive application under discussion unless substantial modifications to the capture pump system are made.

Referring now to FIG. 1 the schematic representation depicts, as noted, a barrier material 10 having a polymeric substrate 12 and any number of layers or coatings (metal oxides, ceramic oxides, polymers, or any other combination such as disclosed in Affinoto U.S. Pat. No. 6,268,695; Yializis U.S. Pat. No. 6,083,628; Shaw et al. U.S. Pat. No. 5,725,909; and Bright et al. U.S. Pat. No. 5,981,059, all of which are incorporated by reference and made a part hereof for their disclosure of specific barrier materials) designated 13A, 13B, 13C, etc. are applied to one side of substrate 12 which is indicative of a typical barrier material construction. The coatings may differ in thickness and composition. For example, barrier material 10 could include a top transparent coating followed by a Barix 200 coating followed by a Planix coating followed by a hard coating applied to substrate 12 as disclosed in the Vacuum Technology & Coating article referenced above. For purposes of this invention, and as known by those skilled in the art, it is to be understood that the layers having thickness in the micron range. In the deposition of the coating there will occur what can be envisioned as "pinholes" or molecular voids in the material through which molecules of any gas of interest can pass. In addition, in the formation of the barrier materials such as in rolling or handling, there occurs stress fractures or micro-cracks through which a gas of interest can diffuse. The "pinholes" and/or "micro-cracks" can be viewed as of "defects" through which the gas of interest diffuses along a transmission path. Obviously, if the gas of interest is an organic gas a larger "pinhole" and/or micro-crack is required than if the gas of interest is a lower molecular weight gas, such as helium.

One of the underpinnings of this invention is the recognition that the transmission of any gas through the barrier material has to follow a tortuous path through the "defects" of each layer (and substrate 12). This is schematically depicted for illustration purposes only in FIG. 1 by transmission paths indicated by flow arrows designated by reference numeral 15 and 16. FIG. 1 is essentially copied from Bright et al. U.S. Pat. No. 5,981,059 (incorporated herein by reference for its disclosure of barrier materials) and reference should be had to the Bright patent for a description of the layers 13A–13H applied over PET substrate 12. FIG. 1 generally shows a barrier layer material of oxides+polymer+oxide. Transmission gas arrow 15 passes through some path in transparent coating 13A and enters coating 13A at some point 15$i$ and passes through coating 13A at some point 15$ii$. It travels at the interface of coatings 13A and 13B and enters coating 13B at some point, shown for illustration purposes only as 15$ii$ and travels through coating 13B through some transmission path or "pinhole" or "micro-crack" until it exits coating 13B emerging at some point 15$iii$. The gas then diffuses along the interface of the coatings 13B and 13C until it reaches a "pinhole" or "micro-crack" in coating 13C, shown for illustration purposes only as point 15$iii$, and passes through coating 13C, etc. The tortuous path is followed until the gas finally exits polymeric substrate 12.

FIG. 1 shows that the transmission of a gas of interest through a barrier material does not typically follow a straight path through the barrier material but instead follows a tortuous path which may travel some distance through the coatings from ingress to egress. Further, some transmission paths may produce a greater flow of gas than other smaller sized transmission paths. This invention uses a mass spectrometer to measure the gas of interest which requires, for its operation, a high vacuum level to produce the desired sensitivities needed to test engineered plastic materials. If the specimen area is of the size referenced in the "Henry paper" cited above (1 cm$^2$). FIG. 1 shows that the measurements of a mass spectrometer can not accurately sense an average gas transmission or permeability characteristics of a barrier material. That is, the size of the area being measured for gas transmission is so small that the "pinhole" or transmission path is either not present or is present and in either instance an unrepresentative reading is given. Accordingly, this invention sets a specimen sealed area schematically indicated by dash line 20 in FIG. 1 through which the gas of interest must pass.

Those skilled in the art will recognize that the size of specimen sealed area 20 is a function of the barrier material (and to a lesser extent the size of the gas of interest) and more particularly the size and number of the transmission paths through the barrier material such as shown by flow paths indicated by reference arrows 15 and 16. In the preferred embodiment for today's barrier materials of interest, this invention sets specimen sealed area 20 to at least 10 cm$^2$ and more preferably to at least 50 cm$^2$ which will produce a test area that will be indicative of an "average" or "uniform" diffusion or transmission of a gas of interest throughout the entire barrier specimen. As will be explained below, a high vacuum sufficient to allow a mass spectrometer to analyze the gases of interest can be drawn on one side of barrier material 10 at sealed specimen area 20 which will not distort or deform or even materially deflect the specimen so as to render it useless. Specifically, a high vacuum (low pressure) is drawn on one side of the barrier material at a level sufficient to allow the mass spectrometer to produce accurate readings for the gas of interest (i.e., partial pressure of any specific gas of interest). The high vacuum thus established is "balanced" by setting the "rough" vacuum on the opposite side of the barrier material to establish a low pressure differential between both sides of the barrier material. The specimen area is now a function of the pressure differential which is variably adjusted as a function of the rough vacuum and can be sized large enough to provide a representative sample, i.e., 10–50 cm$^2$. Thus, the inventive test equipment imposes on the specimen no undue forces or strains which the specimen would not encounter under normal operating conditions of the end product. Note that the continuous flow rate of fresh test gas through the test gas chamber is set and the rough vacuum drawn in the test gas chamber is also set. By continuously flowing fresh test gas, there is a 100% concentration of the gas of interest in the test chamber throughout the testing period. Should any outgassing of the substrate occur, it is swept away.

Figure 2:
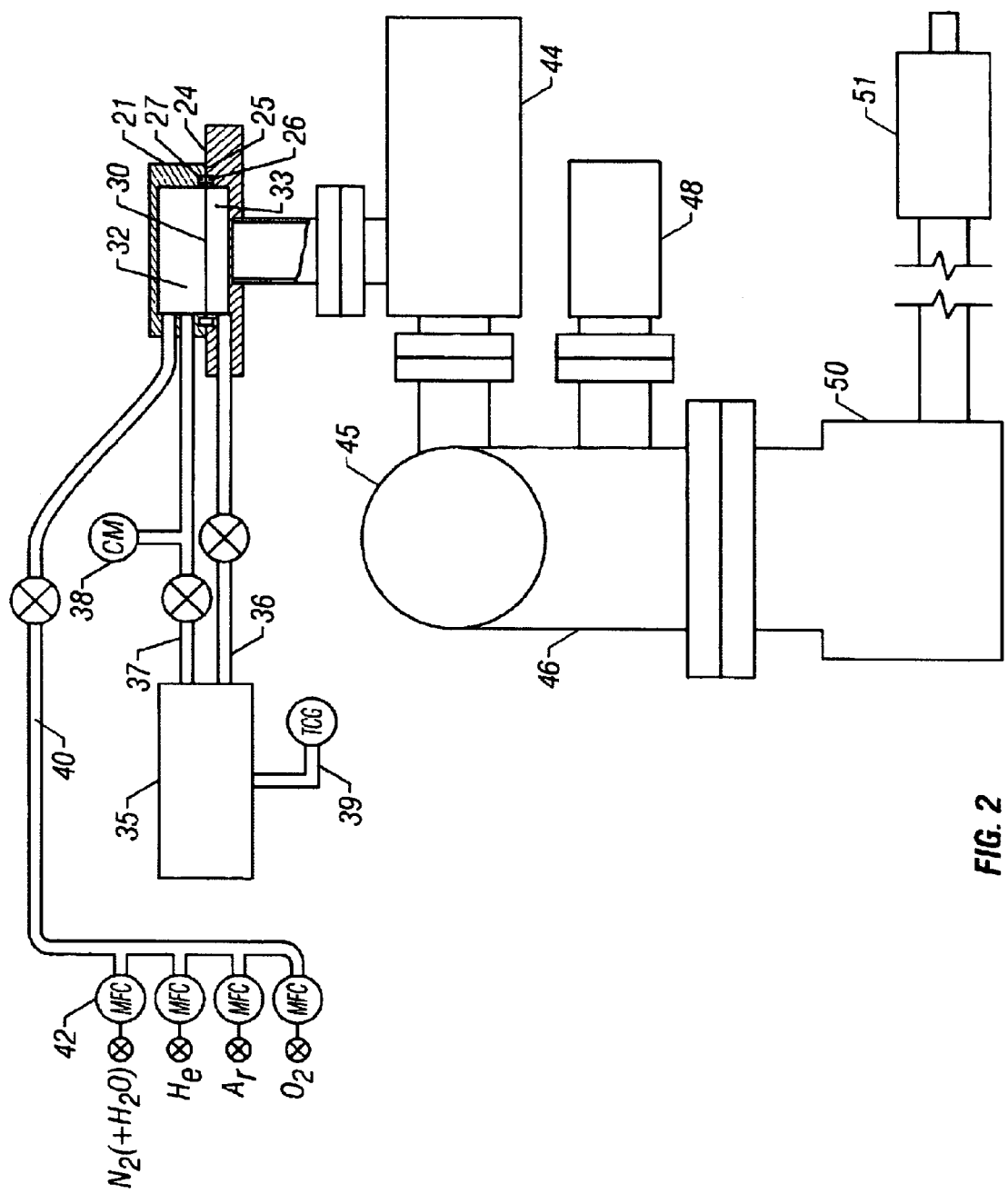
FIG. 2 is a schematic representation of a single chamber test device incorporating the principles of the present invention.
Figure 3:
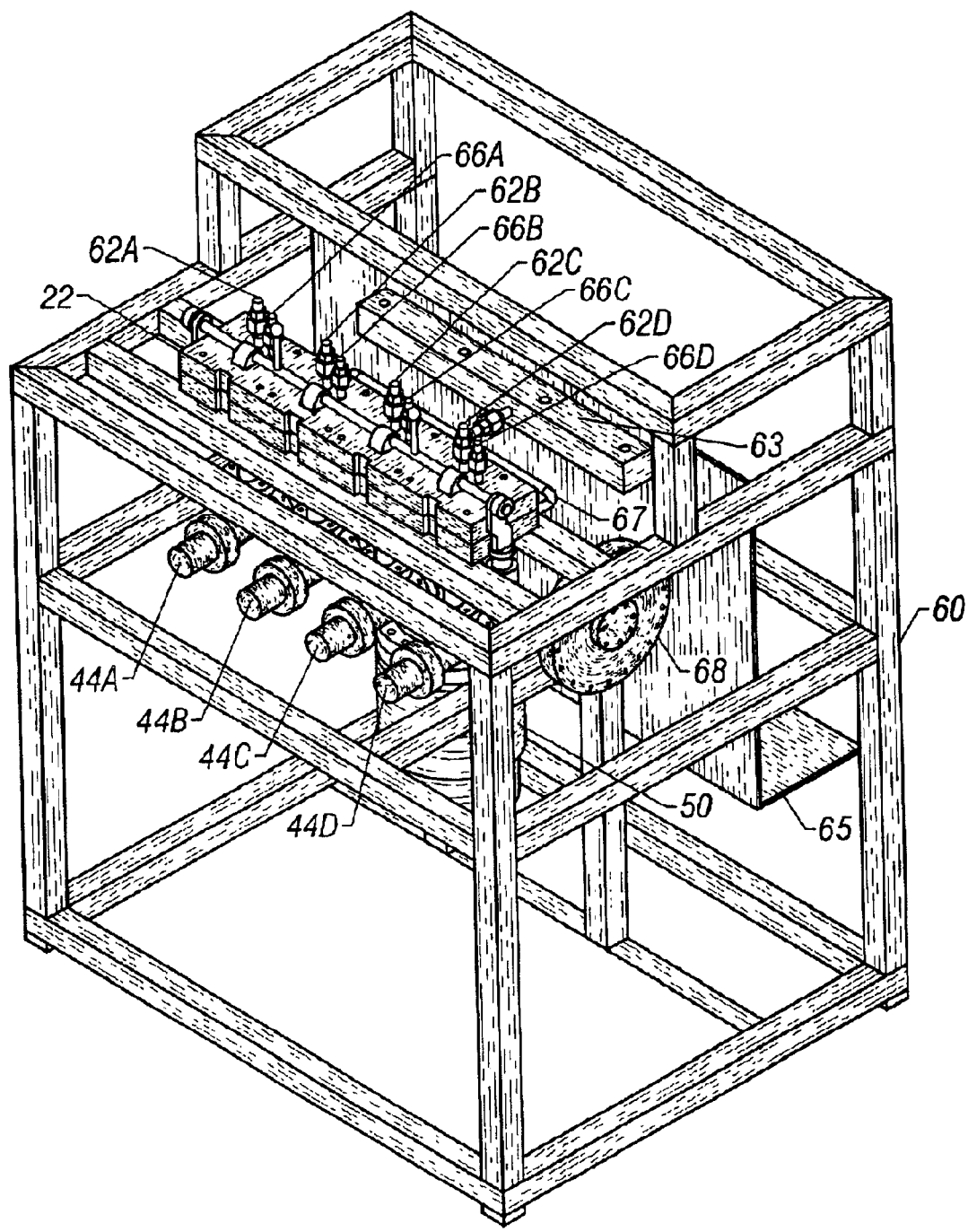
FIG. 3 is a pictorial representation of a portion of a multi-chamber test device constructed in accordance with the principles of the present invention.
Figure 4:
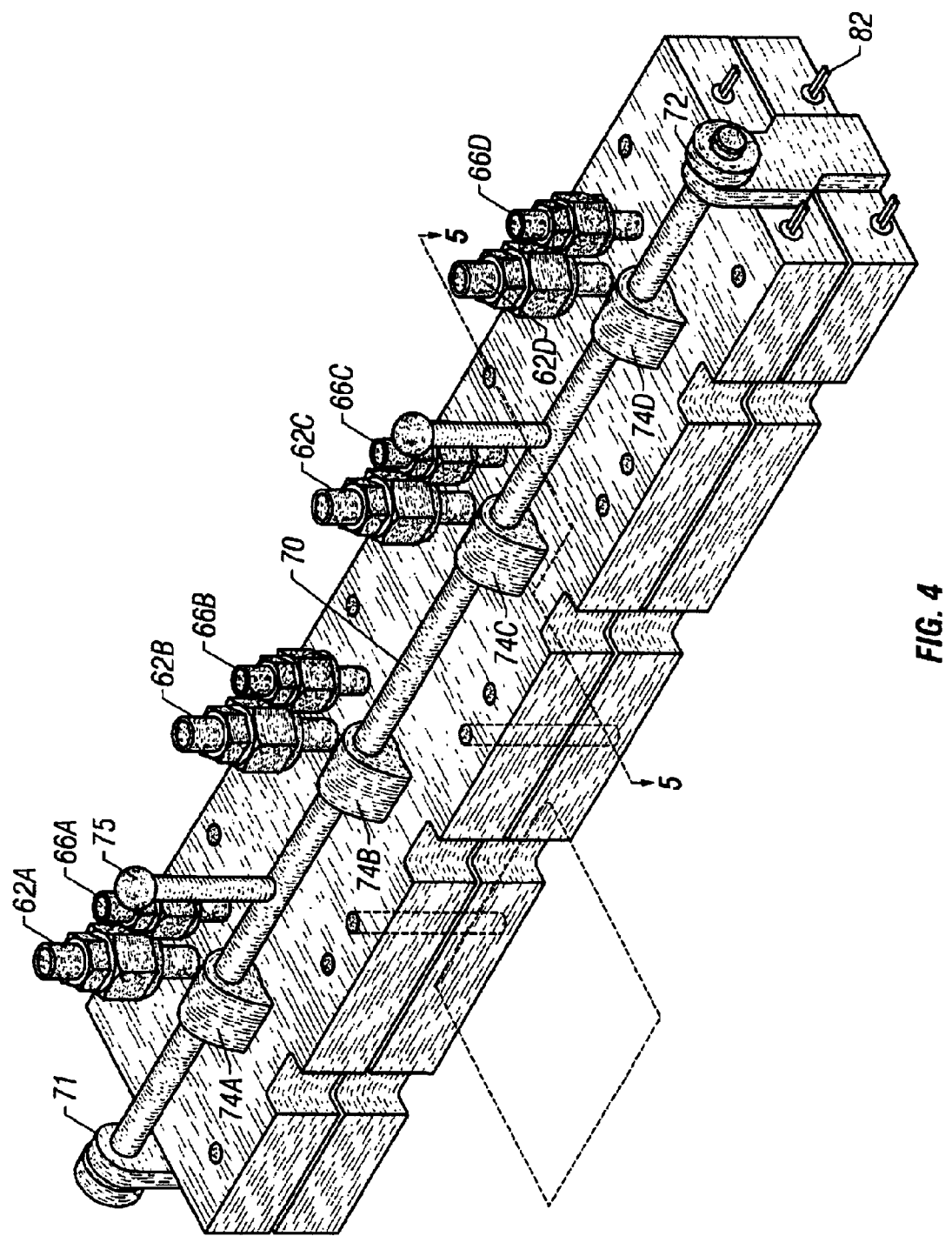
FIG. 4 is a pictorial representation of the multi port sample holder of the device shown in FIG. 3.
Figure 5:
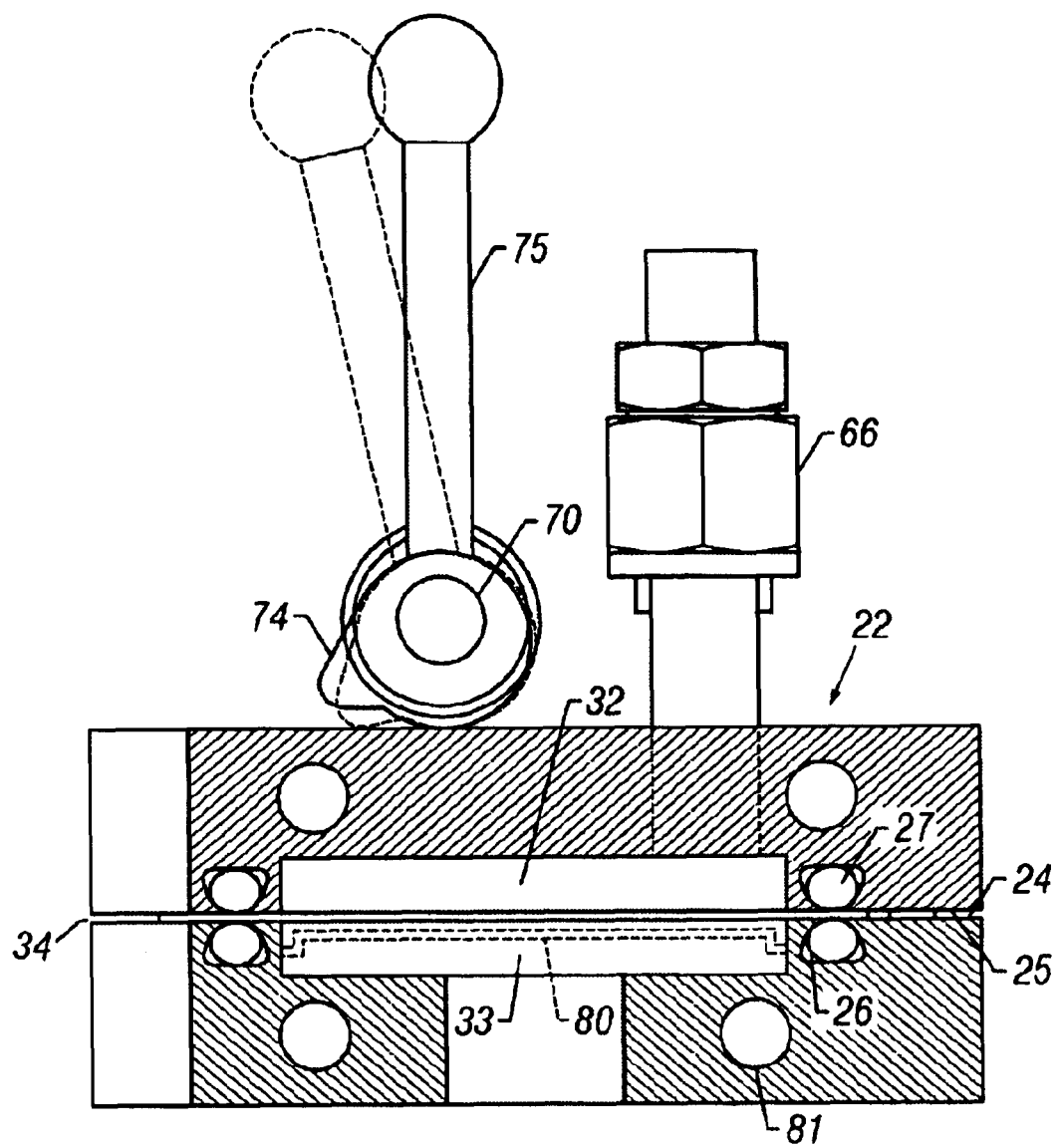
FIG. 5 is a cross-sectioned view of the multi port sample holder shown in FIG. 4 taken along lines 5—5.
Figure 7:
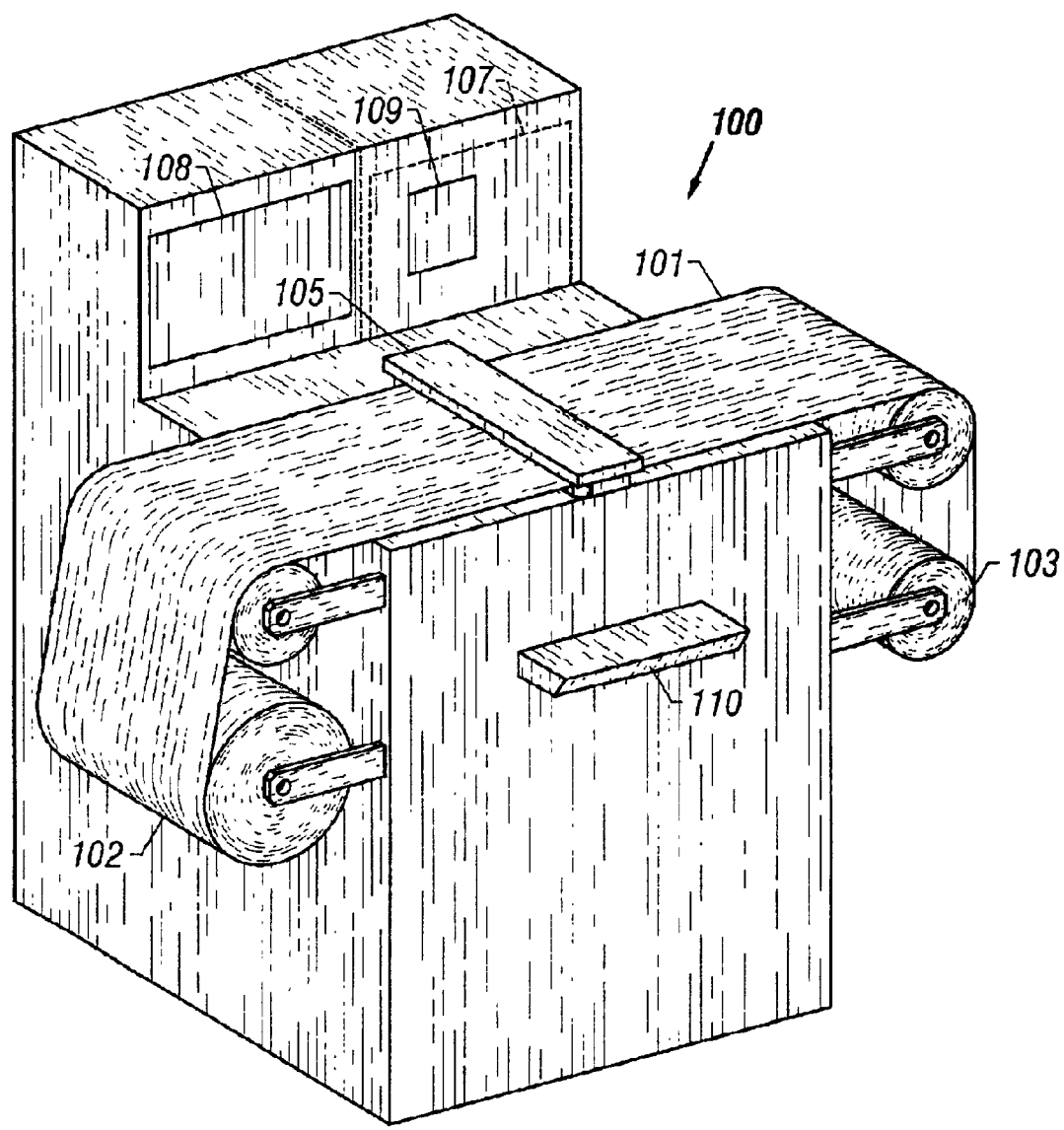
FIG. 7 is a pictorial representation of a production test device incorporating the principles of the present invention.

FIG. 2 is a representation of the permeation or gas transmission measuring instrument basically comprising a test box having a single test port holder 21 and the permeation test instrument partially illustrated in FIGS. 3, 4, and 5 has a vacuum test box which can be viewed as a multi-port holder 22. The permeation test instrument illustrated in FIGS. 3–5 is indicative of the design of a prototype unit and has four ports for simultaneously testing four different gases or, alternatively, for testing the same gas over four different areas of interest 20 to determine either an average transmission rate of a gas of interest or, alternatively, verify that the specimen sealed area 20, is of a size sufficient to produce an average diffusion of a gas of interest through a barrier material coupon 30. That is, one of the functions of the prototype unit is to establish an adequate specimen sealed area 20. A production version of the test instrument which may have a different port configuration than the single or multi-port configuration shown in FIGS. 2 and 3–5, respectively, is illustrated in FIG. 7 and will be discussed later.

Referring now to FIG. 2, there is shown in diagrammatic view the basic components used in all embodiments of the gas transmission test instrument of the present invention. All components are commercially available items known to those skilled in the vacuum pumping art, but their selection and arrangement, as discussed herein, have been chosen to assure relatively trouble free operation of the instrument when used for measuring gas transmission through a barrier material sample or coupon 30.

The test box making up single test port housing 21 has first and second metal flanges 24, 25 in each of which is disposed a continuous first and second O-ring seal 26, 27 (best shown in FIG. 5). As will be clear from the discussion below, the seal integrity for first O-ring seal 26 (forming test gas chamber 32) is not as critical for the seal integrity of second O-ring seal 27 forming measurement chamber 33. Technically, if test gas chamber 32 was at atmospheric or slightly positive pressure, the continuous flow of the test gas would prevent atmospheric air entering test gas chamber 32 and a seal would, strictly speaking, not be required. Similarly, if the test gas chamber 32 was at a slight underpressure, the demands on first seal 26 would be slight, i.e., the seal must be sufficient to draw the slight underpressure. Leakage or seal integrity is not that critical for test gas chamber 32 because of continuous flow of the test gas which will purge any ambient gas entering test gas chamber 32 vis-a-vis the seal. In the preferred embodiment, both first and second seals 26, 27 are identical. It is simply noted that because the demands on the seals are different, other types of seals can be used for test gas chamber 32. However, O-ring seals are preferred in any event because no damage to the sample results from their use.

Sealed between first and second O-ring seals 26, 27 is sample barrier material coupon 30. In the prototype device barrier material coupon 30 had a dimension of approximately 4 inches by 4 inches and first and second O-ring seals 26, 27 are identical to one another and circumscribe a specimen sealed area 20 of approximately 50 cm$^2$. With barrier material coupon 30 sealed in place between first and second O-ring seals 26, 27 the test box forms a test gas chamber 32 (shown as the top chamber in FIG. 2) and a measurement chamber 33 (shown as the bottom chamber in FIG. 2). The only communication between test gas chamber 32 and measurement chamber 33 is barrier material coupon 30, which, by definition, is permeable. For definition, test gas chamber 32 and measurement chamber 33 together form a port 34, which is opened along a parting line defined by metal flanges 24, 25. For the multi-port prototype embodiment, ports 34 and their associated components will be designated by reference letters A, B, C and D following the reference numerals.

A first roughing vacuum pump 35 is provided in valved communication with measurement chamber 33 through measurement chamber roughing line 36. A capacitance manometer 38 is provided in test gas chamber roughing line 37. First roughing vacuum pump 35 is also in communication with test gas chamber 32 through test gas chamber roughing line 37. A vent 39 valved to atmosphere is in fluid communication with first roughing pump 35.

Also in valved communication with test gas chamber 32 is a test gas line 40. Test gas line 40 is adapted to be in communication with any one of a plurality of gases of interest, such as nitrogen, helium, argon, oxygen, water vapor, etc. Rate of flow of any gas of interest in test gas line 40 is controlled by a mass flow controller 42.

A high vacuum valve 44 provides fluid communication between measurement chamber 33 and a header 45 connected to a high vacuum manifold 46. In fluid communication with high vacuum manifold 46 is a mass spectrometer 48. In the prototype (FIGS. 2–6) the mass spectrometer is an MKS/SPECTRA mass spectrometer which is supplied complete with a pc (personal computer) and a monitor (model MicroVision Plus). The MKS spectrometer has a minimum partial pressure sensitivity of less than $2\times10^{-11}$ Torr, and a minimum detectable concentration of less than 80 ppb for all gases except hydrogen (10 ppm). Measurable range of the MKS mass spectrometer is 1–100 amu (atomic mass units). Also in fluid communication with high vacuum manifold 46, is a high vacuum pump 50. In the prototype system, high vacuum pump 50, is a 550 l/s (liters per second) Varian Turbomolecular pump and is backed by a second roughing pump 51 to make the system suitable for $O_2$ service i.e. exhaust to atmosphere. In the prototype system both roughing pumps 35, 51 are Varian dry mechanical scroll pumps. In accordance with the broader definition of the high vacuum pump, a diffusion pump could be substituted for the Turbomolecular pump but the diffusion pump would also be backed by a roughing pump.

It is to be noted that the system on the measurement side, is metal gasket sealed with the exception of the measurement O-ring seal 27 and a seal in the bonnet valve (shown as V5 in FIG. 6) to eliminate any permeation of external gases into the measurement side of the system and contributing to the background noise which the mass spectrometer must differentiate. More specifically, all of the gages and flanges of the test instrument, at least in the measurement side of the instrument, have crushed copper metal gaskets (Conflat® flanges, registered trademark of Varion Corp.— not shown in the drawings) to prevent permeation of gases, specifically lighter gases, such as helium or hydrogen, into the measurement chamber which may otherwise occur with elastomer seals, such as O-rings. This construction coupled with the high vacuum (low pressure) of the constant speed, turbomolecular pump disclosed in the preferred embodiment allow the mass spectrometer to exhibit excellent signal-to-noise ratios to accurately measure the partial pressure of the gas of interest.

The operation of the instrument will be described in detail below. A general overview of operation is to isolate high vacuum pump 50 from measurement chamber 33 and actuate first roughing vacuum pump 35 to pull an equal vacuum in both test gas chamber 32 and measurement chamber 33. High vacuum valve 44 is then opened allowing high vacuum pump 50 to pull a high vacuum in measurement chamber 33 while test gas chamber 32 is at the initial roughing vacuum level. Test gas line 40 is then valved into communication with test gas chamber 32 with rate of flow established by mass flow controller 42 which in turn is set by capacitance manometer 38 to produce a desired pressure differential between test gas chamber 32 and measurement chamber 33. Mass spectrometer 48 then operates in a conventional manner scanning through its measurable range (1–100 amu) to continuously detect in each scan the particular gas of interest. Flow of the gas of interest into and out of test gas chamber 32 is continuous and test gas chamber 32 is maintained at a constant vacuum, although in theory, test gas chamber 32 could reach atmospheric pressure.

The prototype unit constructed included a multi-port sample holder 22 as shown in FIGS. 3, 4, and 5. FIG. 3 shows multi-port sample holder 22 mounted to the vacuum test instrument frame 60 with only portions of the test instrument shown. In the prototype, multi-port sample holder 22 has four ports, 34A–34D, each of which comprises a test gas chamber 32 and a measurement chamber 33 generally in a circular or elliptical configuration (as defined by first and second O-ring seals 26,27). In fluid communication with each test gas chamber 32 is a test gas fitting 62 there being four such fittings designated by reference numeral 62A, 62B, 62C, and 62D. As shown in FIG. 3, each gas fitting 62 connects to a gas manifold 63 which in turn will be connected to a pressurized gas container resting on a ledge 65 in test instrument frame 60, and connected by appropriate valves and mass flow controllers into gas manifold 63 (not shown). Also connected to each test gas chamber 32 is a rough vacuum fitting 66 (66A, 66B, 66C and 66D shown) and a rough vacuum fitting (not shown) is also provided for each measurement chamber 33. All rough vacuum fittings are in fluid communication through appropriate valves to a roughing exhaust manifold 67, a portion of which is shown in FIG. 3. Also shown in FIG. 3 are high vacuum valves designated 44A, 44B, 44C and 44D, high vacuum pump 50 and a mount 68 for mass spectrometer 48.

Referring now to FIG. 4, the sealing mechanism for the prototype is shown to specifically include a central rod 70 mounted in end journals 71, 72 so as to be rotatable therein. At the center of each port, a cam lug 74 is fixedly mounted to central rod 70. An actuating lever 75 extends upwardly from central rod 70. In the prototype, as shown in FIG. 5, manually moving actuating lever 75 rotates central rod 70 within end journals 71, 72 causing cam lug 74 to push first metal flange 24 towards second metal flange 25 thereby deforming O-ring seals 26, 27 into vacuum sealing contact with barrier material coupon 30. Note that the protrusion of cam lug 74 is shaped to cause rod 70 to remain in a stationery locked position once lever 75 has rotated the rod a set angular distance and assures a fixed mechanical deflection of O-rings 26, 27. In the production test instrument, a similar cam arrangement can be used, but central rod 70 would be rotated a set angle by a motor drive or, alternatively, a hydraulic, pneumatic, or an electric drive press arrangement can be employed.

Referring now to FIG. 5, there are drilled openings 81 longitudinally extending through multi-port sample holder 22. Drilled openings 81 are spaced relative to test gas chamber 32 and measurement chamber 33 to optionally provide a source of heat to both chambers 32, 33. In the preferred embodiment, resistance heating elements, or heater rods 82 (commercially selected as "fire-rod" cartridge heaters for the preferred embodiment) are inserted into drilled openings 81. Alternatively, a heated fluid can be caused to be circulated through drilled openings 81 and drilled openings 81 can interconnect with one another to provide a heated manifold or even, conceptually, a cooling manifold for investigating the effects of temperature on gas transmission rates through barrier material coupon 30. Also drawn in dashed line in FIG. 5 and indicated by reference numeral 80 is an optional mesh support which can be fitted into measurement chamber 33 so that mesh support 80 just barely contacts or is slightly spaced from the measurement side surface of barrier material coupon 30 (when O-ring seals 26, 27 are compressed). The function of support 80 is to prevent excessive deflection of barrier material coupon 30 should excessive differential pressure exist between test gas chamber 32 and measurement chamber 33 or should sealed specimen area 20 be significantly increased in size. For example, should sealed area 20 span the width of a sheet roll of barrier material for production testing, support 80 would be used. Any regularly repeating geometrically shaped pattern, grid, or lattice can be used to form support 80, and the size of the geometric pattern is a function of the size of the wire in the mesh or the channel in the lattice. However, the wire, channel, or latticework must be rounded. It will be recognized by those skilled in the art that contact with the grid by barrier material coupon 30 will not interfere with gas flow through the barrier material because a vacuum is used. Special calibration techniques are not required.

The fundamental mechanical components of the system have been discussed above in FIGS. 3, 4, and 5 for the multi-port embodiment. The valving and operation of the system may best be explained by reference to FIG. 6 which schematically lays out the system so that the portion of the drawing shown above test gas chambers 32 controls test gas chambers 32, and that portion of the drawing below the measurement chambers 33 controls the measurement chambers. Where possible, reference numerals used previously in explaining the inventive test instrument will apply to FIG. 6. However, valves will be designated by reference letters for ease of explanation. The only connection between the two chambers (32A–33A, 32B–33B, 32C–33C, 32D–33D) is by valves V5A to V5D which allow both test gas chamber and measurement chamber to be roughed simultaneously before valves V5A–D are closed.

Starting from a closed system, valves V6A to V6D are closed. Roughing pump 51 is turned on and once roughing pump 51 achieves its base pressure, valve V1 is opened and this allows the whole high vacuum manifold 46 including the mass spectrometer chamber, (in fact the entire system downstream of V6) to be pulled to a rough vacuum. Once roughing vacuum is established (and system integrity verified), turbo molecular or high vacuum pump 50 is activated and once at operating speed, ion gage 90 and residual gas analyzer 48 are turned on. Vacuum integrity is verified during rough pumping by a convectron gage 91 (Granville-Phillips convectron gage in preferred embodiment) which is a thermocouple gage (operating as a Wheatstone bridge) having a range from atmosphere down to about $10^{-3}$ Torr. Vacuum integrity under high vacuum is assured by ion gage 90 which has a sensitivity starting at about $10^{-4}$ torr and going to lower pressures.

Calibration of mass spectrometer 48 can be done at this time (if not previously). As indicated in the background, a helium filled ampoule having a quartz membrane can be placed in a calibrated leak chamber 92 and manually valved by valve V9 into communication with mass spectrometer 48. The mass spectrometer looks at the background helium diffused through the quartz membrane of the test ampoule and reads the partial pressure as a function of the NIST standard leak of helium through the quartz membrane. The mass spectrometer is adjusted to be in concurrence with the NIST standard. (Prototype mass spectrometer was calibrated under NIST Test No. 263977-00T210 and NIST ID number is NBSLC210). After calibration, manual valve V9 is closed and helium pumped out of the system by high vacuum pump 50.

Continuing the discussion starting from cold, roughing pump 35 can be turned on at any time and everything is closed with the exception of vent valve V3. The test ports 34A–D are opened and barrier material coupons 30A–D are slid into the ports and lever 75 cammed down to establish, by compression of seals 26, 27, test gas chambers 32 and measurement chambers 33. After positioning the coupons, vent valve V3 is closed and valve V2 is opened to establish a rough vacuum in test gas chambers 32A–D. Simultaneously valves V5A through V5D are opened to establish a rough vacuum in measurement chambers 33A–D. Both sides of the barrier test specimen or diaphragm are simultaneously roughed by the same source of vacuum, i.e., roughing pump 35. Thus there is no deflection or mechanical damage to the barrier because both sides of the barrier specimen have been simultaneously exposed to the same vacuum.

Once base vacuum level is achieved, valves V5A through V5D are closed and valves V6A through V6D are opened. This puts a slightly higher vacuum on the measurement chamber side of the specimen. That is, at the limits of definition, a rough vacuum of $10^{-3}$ Torr exists in the test gas chambers 32A–D and a vacuum of $10^{-4}$ Torr exists in the measurement chambers 33A–D which is not a significant pressure differential. However, in the preferred embodiment application, a vacuum at pressure as low as $10^{-11}$ Torr may be pulled in the measurement chambers. As will be discussed shortly, the mass flow controllers for the gases of interest will be set, not so much for their flow rate, but to establish a pressure differential between the test chamber side of the barrier material coupon and the measurement side of the coupon in the range of approximately 20 or so Torr. At a pressure differential of 20 Torr between the test gas chamber side of the coupon and high vacuum on the measurement side of the coupon, calculations show that for a sealed specimen area 20 of 50 cm$^2$, a force of about 3 pounds will be exerted on the barrier material which is not sufficient to deform the coupon in any plastic way. It should be recognized that a sealed specimen area of 50 cm$^2$ (7.75 in$^2$), has the potential of approximately 115 pounds of force across the sample if exposed to full atmospheric pressure. If the maximum pressure on the test gas side is regulated by capacitance manometer 38 to be less than 75 Torr, then the total force across the sample will be reduced by a factor of 10, i.e., 11.2 lbs at 75 Torr, and so on. Depending on the sample thickness and mechanical properties, a sample pressure of 25 Torr will produce a total pressure across the sample of about 3.7 pounds, which should not plastically deform the coupon in most cases. However, the pressure differential may need to be reduced or a support provided during elevated temperature tests. Obviously, as the pressure differential increases, the time at which saturation or equilibrium of the gas of interest in the barrier material occurs will decrease. However, the inventive system does not necessarily require testing to equilibrium.

With the system now at the pressures specified, a gas of interest is selected. In the preferred embodiment, the gases of interest that have been selected to evaluate are water vapor (the A designation), argon (the "B" designation), helium (the "C" designation), and oxygen (the "D" designation).

The water vapor system includes a container of water shown as reference numeral 94 which is equipped with an agitator and a heater (not shown) which maintains the temperature of the water at 20_C. to 75_C. In the preferred embodiment, a source of nitrogen indicated by reference numeral 95 is supplied to the water container, so that when a vacuum is pulled on the water container the nitrogen will function as a carrier gas bubbling through the water and carrying water vapor to the system. The nitrogen carrying the water vapor can then pass as a gas through the system for evaluation. It is possible for the water container to supply water vapor when a vacuum is pulled on water container 94 without a carrier gas but bubbling a carrier gas (N$_2$) is required to create a high concentration of water vapor in the carrier gas. It is to be recognized that barrier materials 10 with polymeric substrates have an affinity for water (water may comprise as much as 10% of the plastic weight) which is deleterious to their function as OLED panel displays etc. Water is present in the ambient atmosphere as a function of the relative humidity of the atmosphere. Existing test procedures require control of the relative humidity present in the test gas (See Mocon article cited in the Background). The inventive vacuum system has no such constraint. By measuring transmission of water vapor through the barrier specimen it can be determined how long it will take a barrier material to allow a fixed quantity of water to permeate therethrough which is deemed hazardous to the OLED fixed panel display. With the quantity of water transmitted through the barrier material as a function of time known, the relative humidity present in an ambient atmosphere to produce the quantity of water permeated through the barrier material can be calculated and the life of the OLED display determined.

Further, if the OLED display is placed in a highly humid operating environment, its life can also be readily calculated. Special high humidity tests do not have to be conducted.

For discussion purposes, assume the gas of interest selected is oxygen and the mass flow controller, MFCD for oxygen is set at a specified rate sufficient to cause 20 Torr pressure differential to exist between test gas chamber 32D and measurement chamber 33D. Again, the flow rate is not significant. It is set to establish the desired pressure differential. In this connection, there is also provided a manual throttling valve 96 (i.e., butterfly valve) adjacent valve V2 which may be optionally set to adjust the pressure differential in the test port. (Should very high pressure differentials be desired to decrease test time, measurement chambers 32 may be fitted with mesh 80.) Once the rough vacuum is pulled, valve V8D is opened, valve V4 is opened and capacitance manometer 38 is read.

Figure 6:
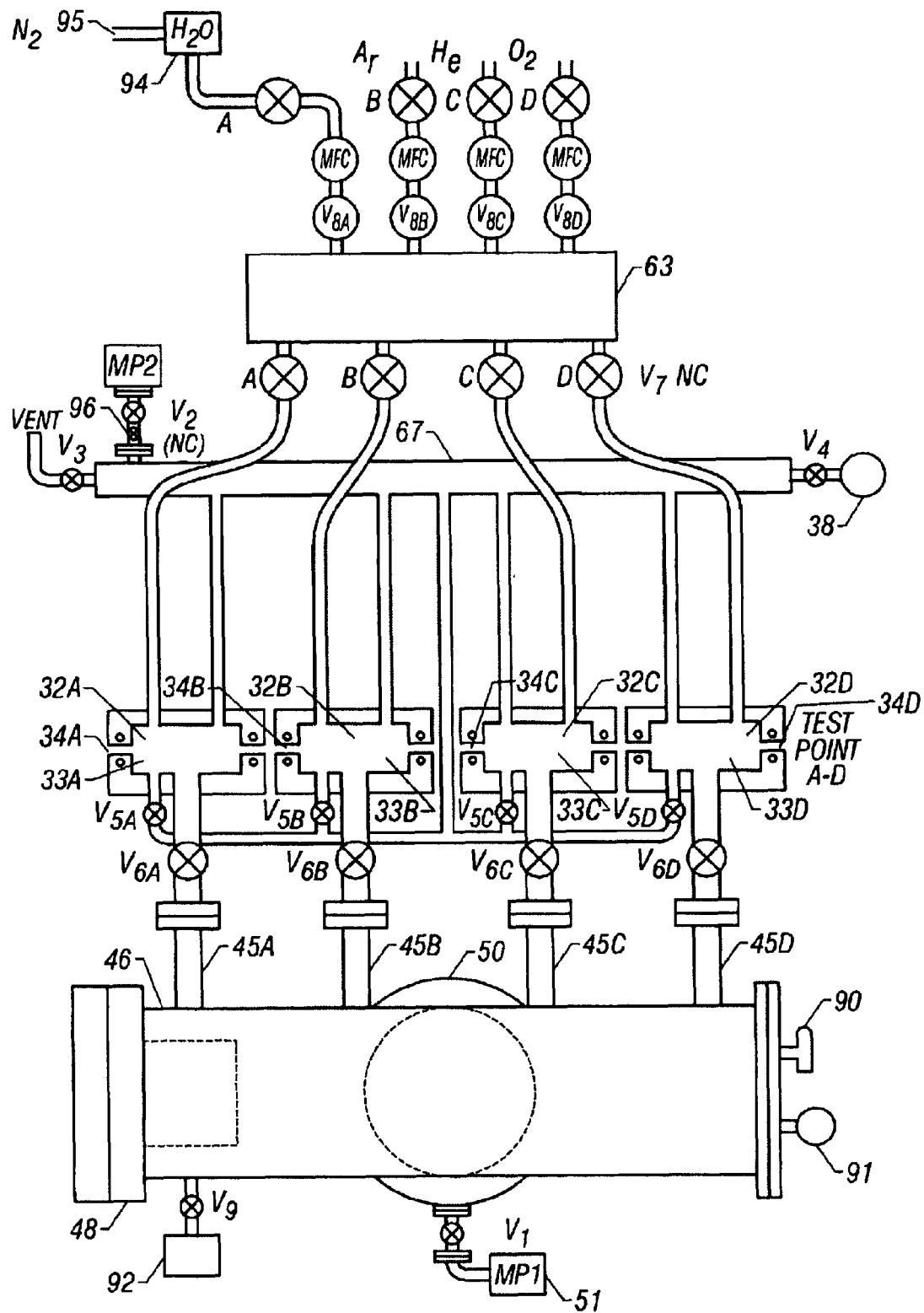
FIG. 6 is a schematic representation of the valving used in the device shown in FIGS. 3–5.

While all the components used in the system are conventional, the selection of several components, such as high vacuum pump 50 is made because of characteristics that render the device suitable for the specific application under consideration. The selection of the capacitance manometer is one of such items. A capacitance manometer is a very sensitive pressure diaphragm gage which is able to read the pressure in the roughing vacuum range and is insensitive to the type of gas. The capacitance manometer includes two varying diaphragms, One is fixed and relatively rigid and the other variable with high vacuum sealed between the two. Vacuum is exposed on the back side of the variable diaphragm so that deflection of the variable diaphragm is measured as a change in capacitance and will register the same reading whether the gas is helium or oxygen. In contrast, Convectron gage 91 has a resistance leg of the Wheatstone bridge in a vacuum with resistance change measured as a function of temperature tied to the conduction characteristics of the gas. Different mass gases conduct temperature differently and difference in readings can occur. This is not a problem for CG gage 91 because of its location and function as shown in FIG. 6.

Based on the reading of capacitance manometer gage 38, throttle valve 96 adjacent valve V2 will be adjusted to establish a desired differential pressure which as indicated above is preferably in the initial range of approximately 20 Torr. Thus, there is a steady state flow of gas continuously through test chamber 32D. The gas is not back filled. There is no depletion because of gas diffusion through barrier material coupon 30. In summary, valves V8 and V7 are opened. Gas is transmitted to test chamber 32D where it is circulated uniformly only on the test gas chamber side of barrier material coupon 30 and exhausted through roughing manifold 67. At the same time, mass spectrometer 48 is being read for the gas of interest in measurement chamber 33D. It is to be appreciated that the pc supplied with the mass spectrometer (not shown in FIGS. 2–6) in combination with a PLC (proportional logic controller—not shown) can also control the actuation of all valves described in FIG. 6 with the exception of those valves specifically designated as manually actuated. In particular, all gage readings are "read" by the pc and in response to the gage readings the valves are actuated. That is, the vacuum integrity is verified through the pc and the valves are systemically actuated as discussed above by the pc and the test monitored by the pc.

The mass spectrometer readings are studied to determine the changes in partial pressure of the gas of interest (in this instance oxygen) to determine when a mass spectrometer peak for oxygen is produced. More particularly and is somewhat conventionally known, the gas of interest flows into barrier material until a saturation or equilibrium level is reached whereat a molecule of gas entering barrier material coupon 30 will equal a molecule of gas leaving the coupon. During the initial portion of the cycle, some portion of the gas of interest will be absorbed into barrier material coupon 30 and some will pass through the coupon. Eventually, the equilibrium state is reached. The mass spectrometer will continuously scan the gas concentrations present in measurement chamber 33D and will continuously record during its scan the concentration or quantity of the gas of interest present. Thus, the output reading of the mass spectrometer will show, as a function of time, a curve having some slope rising to a peak at which the curve levels off. The peak is the equilibrium point and the relatively flat portion of the curve following the peak is indicative of the transmission rate of the gas of interest through the barrier material. This methodology is conventional and the methodology will be followed for the first time any specific barrier material is tested in the inventive test instrument.

To reduce initial test time it is preferred, but not necessary, to mount barrier material coupon 30 with the substrate facing test chamber 32 and the barrier layers facing measurement chamber 33 (assuming the barrier material is conventionally coated with the barrier layers only on one side of the substrate). Because a high vacuum is pulled in measurement chamber 33, any residual gas or water vapor will immediately be withdrawn.

Now the rate of rise of the equilibrium curve is correlated to the gas transmission paths or defects which include micro-cracks and/or "pinholes" present, specifically the number and size of the "defects", in the barrier material as discussed with respect to FIG. 1. Once the initial tests based on equilibrium have been established for any specific barrier material, the start and the rate of the rise of the partial pressure curve as the material moves towards equilibrium, i.e., the slope, can be utilized for acceptance/rejection. Conceptually, the correlation is not that dissimilar to the concept expressed in Mocon U.S. Pat. No. 6,009,743, except the Mocon patent is directed to outgasing requiring a saturated material and the inventive concept is directed to transmission occurring during the time the material is reaching equilibrium. The gas transmission correlation is possible because of the sensitivity of the mass spectrometer. More particularly, it is conceptually possible for the sake of discussion to determine say 10 to 12 seconds after the start of the test that if the barrier material is transmitting gas at a partial pressure of $5 \times 10^{-6}$ Torr, this partial pressure will correlate, for example, to a final equilibrium gas transmission at a partial pressure of $5 \times 10^{-4}$ Torr. Such correlation is based on the initial tests where it is known this reading will correlate to an equilibrium saturation of $5 \times 10^{-4}$ Torr which may or may not be acceptable for the requirements of that particular barrier material. Significantly, the sensitivity of the mass spectrometer allows for the correlation to be modeled at an early stage before equilibrium. That is, in the prior art, not only must the test time wait for the barrier material to be saturated with the gas of interest, but even when saturated the sensitivity of the instrument has to determine how long the curve must progress to equilibrium before the correlation can be drawn. Because the mass spectrometer is much more sensitive than the prior art permeation instruments, the difference is expected to be seconds vs hours and thus significant.

In the preferred embodiment, the gases of interest will be tested in the manner stated. An equilibrium curve will be generated for any specific gas of interest and the specimen sealed area 20 is verified as being correct, i.e., either one port 34 or multiple ports 34 will be used and averaged. Further testing of that specific barrier material will then analyze the critical slope of the subsequent coupons vis-a-vis the initially constructed curve that reached equilibrium. An accept/reject accuracy should be achieved. Further, the gases of interest may be heated by heater elements 82 to increase their activity and a correlation can be made to the heated gas curve relative to the initial curve established at ambient temperatures. Similarly, the pressure differential may be evaluated to establish an optimum pressure differential at which initial test times to reach equilibrium may be reduced.

Figure 8:
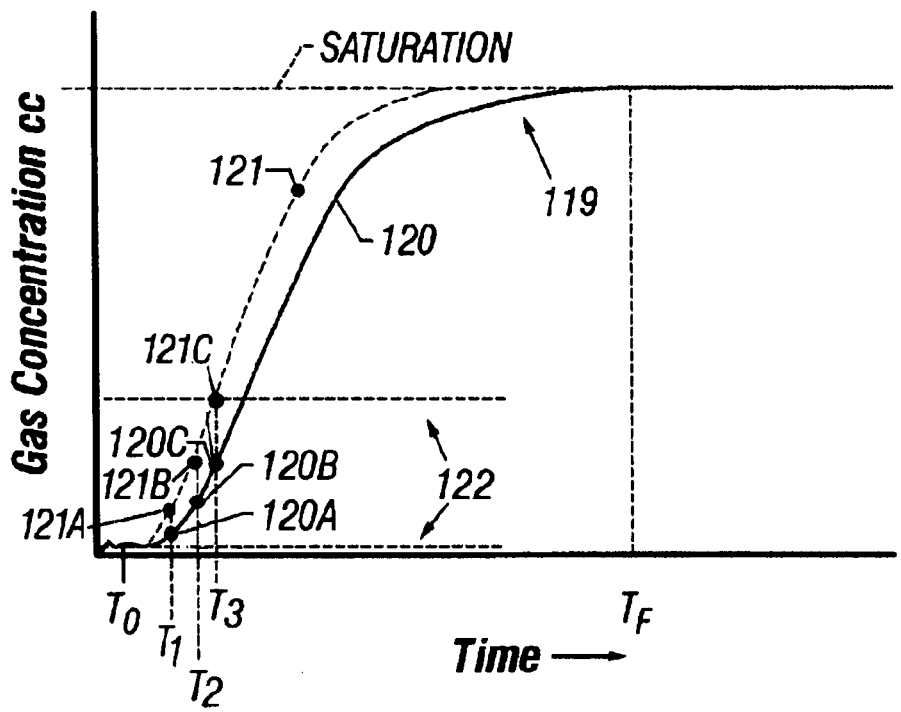
FIG. 8 is a constructed portrayal of a gas transmission curve.

In this regard, reference can be had to FIG. 8 which shows a constructed trace 120 of a gas transmission curve plotted as cc of transmitted gas over time. As discussed above, trace 119 has an initial condition, at time $T_O$ followed by a rising condition designated by reference numeral 120 until a generally flat equilibrium condition occurs at time $T_F$. If the difference in gas transmission between the initial condition $T_O$ and the equilibrium condition at $T_F$ is large enough to approach a magnitude of $10^{-3}$ cc/m$^2$/day, then conventional instruments can detect the permeance of the gas of interest. If the equilibrium condition is a lower order of magnitude, i.e., $10^{-4}$ or lower, detection is not possible. Thus, the inventive instrument, because it has sensitivities at the lower orders of magnitude, can function in a "normal" test environment to determine the gas transmission rate at equilibrium and thus determine permeability of the barrier material. However, this invention is able to discern the gas transmission values during rise portion 120 of the gas transmission curve. For example, the instrument can detect early gas transmission points 120A, 120B, 120C at times $T_1$, $T_2$ and $T_3$ respectively. Early gas transmission points allow the rise portion 120 of the gas transmission curve 119 to be constructed using any one of a number of known curve fitting techniques (i.e., a linear slope can be readily calculated) and the constructed rise portion compared to a stored rise portion (from a prior sample tested to equilibrium) to quickly determine a pass/fail condition. Different samples will exhibit different curves. e.g. 121, similar to 119 but with different slopes. A superior barrier sample will exhibit a gas transmission curve, which rises more slowly, while an inferior barrier will yield a more rapid rise in gas transmission. Alternatively, several readings of gas concentration over time can be compared to a band shown as dotted lines 122 based on statistical analysis of prior samples tested to equilibrium. Readings within the band indicate a "pass". For example, gas concentration readings 121A, 121B, 121C taken at different times, $T_1$, $T_2$ and $T_3$ are compared with values from statistical analysis of prior samples taken at times $T_1$, $T_2$ and $T_3$. Gas concentration 121C is the maximum allowed concentration value (y-axis value) for a pass. Any sample with all gas concentration values below the too horizontal line 122, i.e., within the pass band, at all three test times, $T_1$, $T_2$ and $T_3$ is a pass sample. In practice, a concentration level above zero is commonly measured at the start of the time periods, $T_O$. This value at $T_O$ determines the bottom of the pass band (second dashed line in FIG. 8).

A separate aspect of the invention is the use of helium as the gas of interest followed by correlation of the permeation or transmissability of the helium through the barrier material to any other gas of interest. That is, as described thus far, the test instrument of the invention can determine gas transmission rates of any gas of interest (in the amu range of 1 to 100) by testing over the time it takes for barrier material coupon 30 to reach equilibrium. Once equilibrium is reached, the inventive test instrument records transmission at sensitivities not heretofore reached and allows testing, for the first time, of the newly developed engineered plastic substrates. This is one aspect of the invention. The time for testing at equilibrium is a function of the time it takes for the barrier material to reach equilibrium (i.e., function of pressure differential and barrier material composition). However, correlating the slope of the equilibrium curve, once established, to that observed in subsequent tests allows for testing before the barrier material reaches saturation and will materially reduce test time. This is another aspect of the invention. However, the selection of helium as the test gas of interest for all barrier materials is still another aspect of the invention and its selection may even afford benefits to prior art testing methods.

Figure 9:
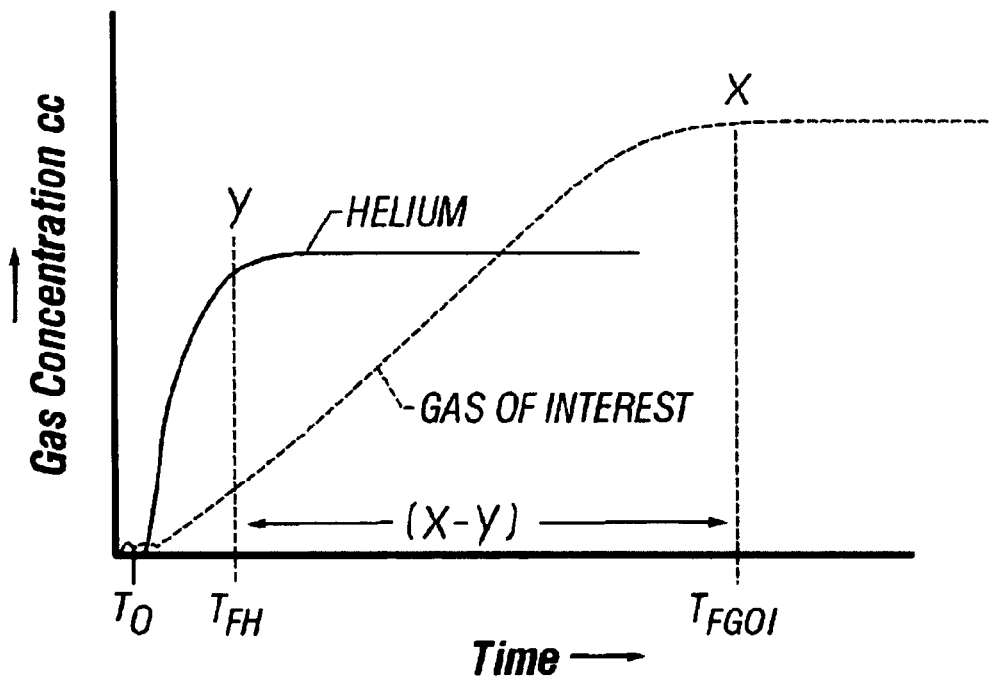
FIG. 9 is a constructed representation of a gas transmission plot of helium superposed over a constructed representation of a gas transmission plot of a gas of interest.

Helium is lighter than other gases of interest which are typically selected (oxygen, water vapor etc) to determine the effectiveness of a barrier material. The molecular activity of helium can be significantly increased by the use of heaters 82 thus increasing its transmissability characteristics through the barrier material. This aspect of the invention recognizes that equilibrium conditions for the helium can be quickly established because the gas readily passes through smaller transmission paths or pinholes which take a longer time for the heavier gases to pass through. Recognizing that the transmission characteristics of any gas of interest through a barrier material is a function of the atomic mass weight of the gas and that transmission paths, i.e., microcracks and/or pinholes—"defects", "open" over time. A correlation of helium to any gas of interest is possible per this separate aspect of the invention. Testing to equilibrium conditions ("Y") occurs over a shorter time span because the barrier material can achieve saturation more quickly with a lighter gas, particularly helium (see FIG. 9). Further, if the helium is excited by heating then equilibrium conditions will be more quickly reached. Thus test time at saturation or equilibrium, for any permeation measuring system is reduced if helium is selected as the gas of interest. The correlation step can take a number of various forms known to those skilled in the art. For example, a gas transmission curve for a given gas of interest from an unsaturated to a saturated condition can be generated. Similarly, the same trace for the same barrier material can be developed with helium and the traces superposed on one another to draw difference correlations. For example, time to reach saturation for a given gas of interest from $T_O$ to $T_{FGO}$ is established as "X", and this correlates, for that barrier material, to a time to reach saturation with helium from $T_O$ to $T_{FH}$ of "X-Y". See, for example, FIG. 9.

However, the inventive test instrument achieves specific results with helium as the gas of interest which may or are not be possible with prior art instruments. First, the sensitivity of the mass spectrometer allows for a correlation level not possible with prior art permeation measurement instruments. Without the sensitivity of the mass spectrometer, correlation conceivably may not be possible with prior art instruments. Significantly, because the mass spectrometer is calibrated on the basis of helium transmission through a quartz membrane, an absolute measurement or at least a measurement of the helium correlated to a NIST standard is obtained. The correlation of the gas of interest to the traismissablity of helium through the barrier material is thus based or referenced to a NIST standard indicative of an absolute measurement. Because the mass spectrometer is calibrated to a NIST standard, the helium test readings of the mass spectrometer are absolute. Importantly, helium is inert and non-invasive. The properties of the barrier material will not be affected by the transmission of helium therethrough which cannot be absolutely stated for other gases of interest. That is transmitting a gas of interest through the barrier material to achieve say saturation could adversely affect the life of that display that comes from the saturated barrier material. Thus the barrier material can be used for production purposes if the transmission gas is helium.

In summary of this aspect of the invention, helium, being inert and lighter than other gases of interest, will achieve equilibrium condition significantly quicker than other gases of interest. Thus, if full testing to equilibrium is required, testing with helium will significantly reduce the test time. Importantly, if acceptance/rejection testing is desired, (where the slope of the curve at its initiation is analyzed), 100% production testing now becomes feasible.

A production test unit 100 is illustrated in FIG. 7. In this embodiment, the barrier material is in sheet form 101 unwound from a pay-out reel 102, tested and collected on a take-up reel 103. Roll rotation is indexed so that roll testing occurs at set longitudinal increments along the length of the sheet. A multi-port or, preferably, a single port holder 105 extends from one sheet edge width to the other sheet edge width. The test gas chambers and measurement chambers span substantially the width of the sheet. The port holder 105 is automated so it can release barrier sheet 101 for indexing by rotation of take-up reel 103 and automatic clamping. Not only the mass spectrometer but also the pumps and the valves illustrated in FIG. 6 are controlled by a PLC/personal computer 107 with a display monitor 108. The sequence for operating the instrument as described for FIG. 6 lends itself readily to automated control vis-a-vis personal computer 107. Personal computer 107 can have a touch pad controller 109 as well as keyboard 110 for typing in commands. Preferably, touch pad 108 accesses a menu depicted on display 108, so the instrument is menu driven in an intuitive manner. Personal computer 107 maintains a record of each roll of barrier material and a printer can be attached to personal computer 107 if a hard record copy is desired.

The invention has been described with reference to a preferred and alternative embodiments. Obviously, modifications and alterations will suggest themselves to those skilled in the art upon reading and understanding the Detailed Description set forth above. For example, the test gas is disclosed as being continuously metered through the test gas chamber but it is conceivable that a pulsing of the test gas may produce equivalent results. Similarly, the measurement chamber could be pulsed and the mass spectrometer measurements synchronized with the pulses. However, such an arrangement which can be viewed as a variation of "continuous" is not preferred. It is intended to include all such modifications and alterations insofar as they come within the range of the present invention.

Having thus defined the invention, it is claimed:

1. A method for determining the gas transmission rate through a barrier material comprising the steps of:
   a) providing a sealable box within which at least a portion of said material is placed;
   b) sealing said material within said box to form a test gas chamber extending from one side of said material and a measurement chamber extending from the opposite side of said material, said measurement chamber encompassing a sealed area of said material sufficient to allow uniform diffusion of a gas through said material;
   c) continuously metering a set quantity of said gas into and out of said test gas chamber by controlling a rough vacuum to determine the concentration of said gas in said test gas chamber as a function of time;

d) drawing a vacuum in said measurement chamber by a molecular vacuum pump to a final vacuum of at least about $2 \times 10^{-4}$ Torr;

e) providing a mass spectrometer in direct valved communication with said measurement chamber; and f) determining the transmission rate of said gas through said material by partial pressure readings of said mass spectrometer.

2. The method of claim 1 further including the step of initially calibrating said mass spectrometer to a national standard indicative of an absolute permeation measurement to establish an absolute gas transmission rate through said barrier material in step (f).

3. The method of claim 2 further including the step of verifying said measurement chamber against leakage at the final vacuum levels of said measurement chamber.

4. The method of claim 3 further including the step of heating said measurement and test gas chambers to a set level whereby the excitation of and the diffusion of said gas into said material is enhanced.

5. The method of claim 2 further including the step of providing a roughing vacuum pump valved into fluid communication with said gas and said test gas chamber and said gas is liquid water in a heated, agitated container connected to said roughing pump, said roughing pump causing water vapor to be supplied to said test gas chamber and said mass spectrometer measuring water vapor concentration diffused into said measurement chamber and determining the ability of said material to resist permeation of humidity present under normal operating conditions of said material.

6. The method of claim 3 wherein said material includes a substrate with a plurality of barrier coatings applied to a substrate surface and said gas may comprise any elemental gas or combination thereof.

7. The method of claim 6 wherein said gas has an atomic mass lower than about 50 including oxygen and water vapor and combinations thereof.

8. The method of claim 7 wherein said gas is an inert gas including argon, helium, and combinations thereof.

9. The method of claim 8 wherein said gas is helium and a correlation step is performed establishing a relationship between the diffusion rate of helium through said material and the diffusion of a gas under study through said material.

10. The method of claim 2 further including the step of supporting said material against excessive deflection into said measurement chamber.

* * * * *